United States Patent [19]

Kraus

[11] Patent Number: 5,523,225
[45] Date of Patent: Jun. 4, 1996

[54] DNA SEQUENCE ENCODING HUMAN CYSTATHIONINE β-SYNTHASE

[75] Inventor: Jan P. Kraus, Littleton, Colo.

[73] Assignee: Regents of the University of Colorado, Boulder, Colo.

[21] Appl. No.: 120,960

[22] Filed: Sep. 13, 1993

[51] Int. Cl.⁶ .............................. C12N 5/10; C12N 1/21; C12N 1/19; C12N 15/60; C12N 15/63
[52] U.S. Cl. .................... 435/240.1; 435/172.3; 435/320.1; 435/252.3; 435/252.33; 435/232; 536/23.2
[58] Field of Search ................ 536/23.2; 435/252.3, 435/252.33, 240.1, 320.1, 172.3

[56] References Cited

U.S. PATENT DOCUMENTS 4,965,188  10/1990  Mullis et al. ........................ 435/6

OTHER PUBLICATIONS

Kraus (1990) in "Molecular Genetics of Chromosome 21 and Down Syndrome", eds. Patterson et al. New York: Wiley–Liss, Inc., pp. 201–214.
Kraus (1987) Methods in Enzymology 143: 388–394.
Skovby et al. (1984) Am. J. Hum. Genet.36: 452–459.
Kozich et al. 1992 Human Mutation 1 (2) 113–123.
Wahl et al. (1987) Methods in Enzym. 152: 415–423.
Kraus et al (1993) Human Mol. Genet. 2 1633–1638.
Micrendorf et al (1987) Methods in Enzym. 152 458–469.
Griffiths et al. (1977) Eur. J. Biochem.
Kraus et al (1986) Proc. Nat. Acad Sci, USA 83: 2047–2051.
Skovby et al. (1984) J. Biol. Chem. 259: 583–587.
Krauz et al (1990) Proc. Nat. Acad. Sci. USA 87: 6629–6633.
Ono et al (1988) J. Bacteriol. 170:5883–5889.
Frohman et al. (1988) Proc. Nat. Acad Sci, USA. 85: 8998–9002.
Ono et al (1992) Current Genet. 21 285–289.

*Primary Examiner*—Robert A. Wax
*Assistant Examiner*—G. E. Bugaisky
*Attorney, Agent, or Firm*—Frederick W. Pepper

[57] ABSTRACT

Disclosed is a purified and isolated DNA sequence encoding human cystathionine β-synthase. Also disclosed is a purified and isolated human cystathionine β-synthase encoded by this DNA sequence. Included is a composition of human cystathionine β-synthase in a pharmacologically acceptable carrier for treating a human suffering from homocystinuria. Also provided are methods of screening human patients to detect mutations in the cystathionine β-synthase gene.

5 Claims, 7 Drawing Sheets

TGCAGGGCCA GGACGCACGT TTCAAGCTCA TCAGTAAAGG TTCCTTAAAT TCCCGAAGCA

AGAAGTTAAC CAAGTAAAAC AGCATCGGAA CACCAGGATC CCATGACAGA TTCTGTTGTC

ACGTCTCCTT ACAGAGTTTG AGCGGTGCTG AACTGTCAGC ACCATCTGTC CGGTCCCAGC

```
ATG CCT TCT GAG ACC CCC CAG GCA GAA GTG GGG CCC ACA GGC TGC CCC
Met Pro Ser Glu Thr Pro Gln Ala Glu Val Gly Pro Thr Gly Cys Pro
 1           5              10                 15

CAC CGC TCA GGG CCA CAC TCG GCG AAG GGG AGC CTG GAG AAG GGG TCC
His Arg Ser Gly Pro His Ser Ala Lys Gly Ser Leu Glu Lys Gly Ser
            20              25                 30

CCA GAG GAT AAG GAA GCC AAG GAG CCC CTG TGG ATC CGG CCC GAT GCT
Pro Glu Asp Lys Glu Ala Lys Glu Pro Leu Trp Ile Arg Pro Asp Ala
            35              40                 45

CCG AGC AGG TGC ACC TGG CAG CTG GGC CGG CCT GCC TCC GAG TCC CCA
Pro Ser Arg Cys Thr Trp Gln Leu Gly Arg Pro Ala Ser Glu Ser Pro
            50              55                 60

CAT CAC CAC ACT GCC CCG GCA AAA TCT CCA AAA ATC TTG CCA GAT ATT
His His His Thr Ala Pro Ala Lys Ser Pro Lys Ile Leu Pro Asp Ile
 65             70              75                 80

CTG AAG AAA ATC GGG GAC ACC CCT ATG GTC AGA ATC AAC AAG ATT GGG
Leu Lys Lys Ile Gly Asp Thr Pro Met Val Arg Ile Asn Lys Ile Gly
            85              90                 95

AAG AAG TTC GGC CTG AAG TGT GAG CTC TTG GCC AAG TGT GAG TTC TTC
Lys Lys Phe Gly Leu Lys Cys Glu Leu Leu Ala Lys Cys Glu Phe Phe
            100             105                110

AAC GCG GGC GGG AGC GTG AAG GAC CGC ATC AGC CTG CGG ATG ATT GAG
Asn Ala Gly Gly Ser Val Lys Asp Arg Ile Ser Leu Arg Met Ile Glu
            115             120                125

GAT GCT GAG CGC GAC GGG ACG CTG AAG CCC GGG GAC ACG ATT ATC GAG
Asp Ala Glu Arg Asp Gly Thr Leu Lys Pro Gly Asp Thr Ile Ile Glu
            130             135                140

CCG ACA TCC GGG AAC ACC GGG ATC GGG CTG GCC CTG GCT GCG GCA GTG
Pro Thr Ser Gly Asn Thr Gly Ile Gly Leu Ala Leu Ala Ala Ala Val
145             150             155                160

AGG GGC TAT CGC TGC ATC ATC GTG ATG CCA GAG AAG ATG AGC TCC GAG
Arg Gly Tyr Arg Cys Ile Ile Val Met Pro Glu Lys Met Ser Ser Glu
            165             170                175

AAG GTG GAC GTG CTG CGG GCA CTG GGG GCT GAG ATT GTG AGG ACG CCC
Lys Val Asp Val Leu Arg Ala Leu Gly Ala Glu Ile Val Arg Thr Pro
            180             185                190
```

FIG. 1A

```
ACC AAT GCC AGG TTC GAC TCC CCG GAG TCA CAC GTG GGG GTG GCC TGG
Thr Asn Ala Arg Phe Asp Ser Pro Glu Ser His Val Gly Val Ala Trp
        195                 200                 205

CGG CTG AAG AAC GAA ATC CCC AAT TCT CAC ATC CTA GAC CAG TAC CGC
Arg Leu Lys Asn Glu Ile Pro Asn Ser His Ile Leu Asp Gln Tyr Arg
        210                 215                 220

AAC GCC AGC AAC CCC CTG GCT CAC TAC GAC ACC ACC GCT GAT GAG ATC
Asn Ala Ser Asn Pro Leu Ala His Tyr Asp Thr Thr Ala Asp Glu Ile
225             230                 235                     240

CTG CAG CAG TGT GAT GGG AAG CTG GAC ATG CTG GTG GCT TCA GTG GGC
Leu Gln Gln Cys Asp Gly Lys Leu Asp Met Leu Val Ala Ser Val Gly
                245                 250                 255

ACG GGC GGC ACC ATC ACG GGC ATT GCC AGG AAG CTG AAG GAG AAG TGT
Thr Gly Gly Thr Ile Thr Gly Ile Ala Arg Lys Leu Lys Glu Lys Cys
            260                 265                 270

CCT GGA TGC AGG ATC ATT GGG GTG GAT CCC GAA GGG TCC ATC CTC GCA
Pro Gly Cys Arg Ile Ile Gly Val Asp Pro Glu Gly Ser Ile Leu Ala
        275                 280                 285

GAG CCG GAG GAG CTG AAC CAG ACG GAG CAG ACA ACC TAC GAG GTG GAA
Glu Pro Glu Glu Leu Asn Gln Thr Glu Gln Thr Thr Tyr Glu Val Glu
        290                 295                 300

GGG ATC GGC TAC GAC TTC ATC CCC ACG GTG CTG GAC AGG ACG GTG GTG
Gly Ile Gly Tyr Asp Phe Ile Pro Thr Val Leu Asp Arg Thr Val Val
305             310                 315                     320

GAC AAG TGG TTC AAG AGC AAC GAT GAG GAG GCG TTC ACC TTT GCC CGC
Asp Lys Trp Phe Lys Ser Asn Asp Glu Glu Ala Phe Thr Phe Ala Arg
                325                 330                 335

ATG CTG ATC GCG CAA GAG GGG CTG CTG TGC GGT GGC AGT GCT GGC AGC
Met Leu Ile Ala Gln Glu Gly Leu Leu Cys Gly Gly Ser Ala Gly Ser
                340                 345                 350

ACG GTG GCG GTG GCC GTG AAG GCT GCG CAG GAG CTG CAG GAG GGC CAG
Thr Val Ala Val Ala Val Lys Ala Ala Gln Glu Leu Gln Glu Gly Gln
            355                 360                 365

CGC TGC GTG GTC ATT CTG CCC GAC TCA GTG CGG AAC TAC ATG ACC AAG
Arg Cys Val Val Ile Leu Pro Asp Ser Val Arg Asn Tyr Met Thr Lys
        370                 375                 380

TTC CTG AGC GAC AGG TGG ATG CTG CAG AAG GGC TTT CTG AAG GAG GAG
Phe Leu Ser Asp Arg Trp Met Leu Gln Lys Gly Phe Leu Lys Glu Glu
385             390                 395                     400

GAC CTC ACG GAG AAG AAG CCC TGG TGG TGG CAC CTC CGT GTT CAG GAG
Asp Leu Thr Glu Lys Lys Pro Trp Trp Trp His Leu Arg Val Gln Glu
                405                 410                 415
```

FIG. 1B

```
CTG GGC CTG TCA GCC CCG CTG ACC GTG CTC CCG ACC ATC ACC TGT GGG
Leu Gly Leu Ser Ala Pro Leu Thr Val Leu Pro Thr Ile Thr Cys Gly
            420                 425                 430

CAC ACC ATC GAG ATC CTC CGG GAG AAG GGC TTC GAC CAG GCG CCC GTG
His Thr Ile Glu Ile Leu Arg Glu Lys Gly Phe Asp Gln Ala Pro Val
            435                 440                 445

GTG GAT GAG GCG GGG GTA ATC CTG GGA ATG GTG ACG CTT GGG AAC ATG
Val Asp Glu Ala Gly Val Ile Leu Gly Met Val Thr Leu Gly Asn Met
            450                 455                 460

CTC TCG TCC CTG CTT GCC GGG AAG GTG CAG CCG TCA GAC CAA GTT GGC
Leu Ser Ser Leu Leu Ala Gly Lys Val Gln Pro Ser Asp Gln Val Gly
465                 470                 475                 480

AAA GTC ATC TAC AAG CAG TTC AAA CAG ATC CGC CTC ACG GAC ACG CTG
Lys Val Ile Tyr Lys Gln Phe Lys Gln Ile Arg Leu Thr Asp Thr Leu
            485                 490                 495

GGC AGG CTC TCG CAC ATC CTG GAG ATG GAC CAC TTC GCC CTG GTG GTG
Gly Arg Leu Ser His Ile Leu Glu Met Asp His Phe Ala Leu Val Val
            500                 505                 510

CAC GAG CAG ATC CAG TAC CAC AGC ACC GGG AAG TCC AGT CAG CGG CAG
His Glu Gln Ile Gln Tyr His Ser Thr Gly Lys Ser Ser Gln Arg Gln
            515                 520                 525

ATG GTG TTC GGG GTG GTC ACC GCC ATT GAC TTG CTG AAC TTC GTG GCC
Met Val Phe Gly Val Val Thr Ala Ile Asp Leu Leu Asn Phe Val Ala
            530                 535                 540

GCC CAG GAG CGG GAC CAG AAG T GAAGTCCGGA GCGCTGGGCG GTGTGGAGCG
Ala Gln Glu Arg Asp Gln Lys
545                 550

GGCCCGCCAC CCTTGCCCAC TTCTCCTTCG CTTTCCTGAG CCCTAAACAC ACGCGTGATT

GGTAACTGCC TGGCCTGGCA CCGTTATCCC TGCACACGGC ACAGAGCATC CGTCTCCCCT

CGTTAACACA TGGCTTCCTA AATGGCCCTG TTTACGGCCT ATGAGATGAA ATATGTGATT

TTCTCTAATG TAACTTCCTC TTAGGATGTT TCACCAAGGA AATATTGAGA GAGAAGTCGG

CCAGGTAGGA TGAACACAGG CAATGACTGC GCAGAGTGGA TTAAAGGCAA AAGAGAGAAG

AGTCCAGGAA GGGGCGGGGA GAAGCCTGGG TGGCTCAGCA TCCTCCACGG GCTGCGCGTC

TGCTCGGGGC TGAGCTGGCG GGACGAGTTT GCGTGTTTGG GTTTTTTAAT TGAGATGAAA

TTCAAATAAC CTAAAAATCA ATCACTTGAA AGTGAACAAT CAGCGGCATT TAGTACATCC

AGAAAGTTGT GTAGGCACCA CCTCTGTCAC GTTCTGGAAC ATTCTGTCAT CACCCCGTGA

AGCAATCATT TCCCCTCCCG TCTTCCTCCT CCCCTGGCAA CTGCTGTCGA CTTTGTGTCT

CTGTTGTCTA AAATAGGTTT TCCCTGTTCT GGACATTTCA TATAAATGGA ATCACACAAA

AAAAAAAAAA AAAAAAA
```

FIG. 1C

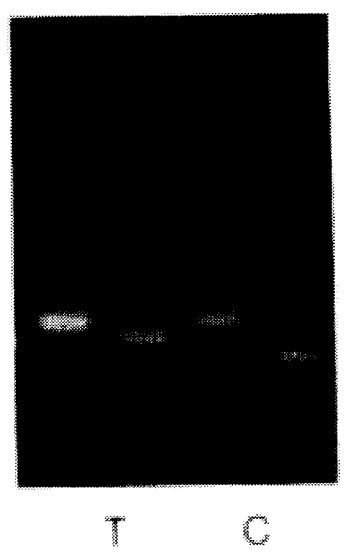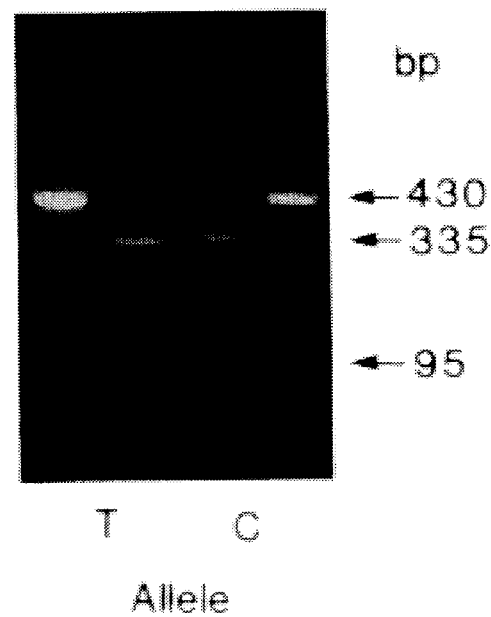
FIG. 3

DNA SEQUENCE ENCODING HUMAN CYSTATHIONINE β-SYNTHASE

The U.S. Government has a paid-up license in this invention and the right in limited circumstances to require the patent owner to license others on reasonable terms as provided for by the terms of Grant No. HD26651 awarded by the National Institute of Child Health and Human Development.

FIELD OF THE INVENTION

The present invention relates to the DNA sequence encoding human cystathionine β-synthase which can be used to produce the synthase by recombinant techniques and methods for detecting and treating patients suffering from deficiency of the synthase.

BACKGROUND OF THE INVENTION

Methionine metabolism occupies a central role in cellular chemistry. The metabolic and regulatory importance of its chief product, S-adenosylmethionine (AdoMet), has long been known, and includes such biologically important functions as methylation, polyamine biosynthesis, side-chain donation, and allosteric enzyme regulation (Castoni et al., *The Biochemistry of Adenosylmethionine*, Columbia University Press, New York, pp.557–577 (1977)). The most frequent metabolic fate of AdoMet is transmethylation. This reaction forms homocysteine, which may be either recycled to methionine by remethylation (Finkelstein et al., *J. Biol. Chem.*, 259, 9508–9513 (1984)) or used to synthesize cysteine by transsulfuration (Mudd et al., *The Metabolic Basis of Inherited Disease*, 6th Ed. McGraw-Hill, New York, pp. 693–734 (1989)). Each of these pathways consumes about half of the intracellular homocysteine, thus they account for the metabolism of all of this metabolic byproduct Finkelstein et al., *J. Biol. Chem.*, 259, 9508–9513 (1984; and, Mudd et al., *The Metabolic Basis of Inherited Disease*, 6th Ed. McGraw-Hill, New York, pp. 693–734 (1989)).

Cystathionine β-synthase (EC 4.2.1.22) (CBS) catalyzes the first irreversible step of homocysteine transsulfuration. This enzyme conjugates homocysteine and serine forming cystathionine, which is subsequently converted into cysteine and α-ketobutyrate in the cystathionine γ-lyase reaction (Mudd et al., *The Metabolic Basis of Inherited Disease*, 6th Ed. McGrawHill, New York, pp. 693–734 (1989)). Pyridoxal 5'-phosphate is a cofactor for these reactions (Kraus et al., *J. Biol. Chem.*, 253, 6523–6528 (1978) and AdoMet enhances the affinity of the enzyme for homocysteine by allosteric activation (Roper et al., *Arch. Biochem. Biophys.*, 298, 514–521 (1992)). Posttranslational proteolysis similarly affects the affinity of the synthase for homocysteine (Skovby et al., *J. Biol. Chem.*, enzyme responds to joint administration of glucocorticoids and cyclic AMP enhancers (Goss, *J. Cell. Sci.*, 82, 309–320 (1986)). These regulatory parameters are consistent with its role as a committed step in a branch-point of metabolism.

Deficiency of synthase in humans is the leading cause of homocystinuria (Mudd et al., *The Metabolic Basis of Inherited Disease*, 6th Ed. McGraw-Hill, New York, pp. 693–734 (1989)). Untreated patients develop a number of phenotypic traits which include skeletal abnormalities, dislocated optic lenses, mild to profound mental retardation, and vascular disorders (Mudd et al., *The Metabolic Basis of Inherited Disease*, 6th Ed. McGraw-Hill, New York, pp. 693–734 (1989)). Some patients respond to vitamin $B_6$ administration while others are unresponsive to this therapeutic intervention (Mudd et al., *The Metabolic Basis of Inherited Disease*, 6th Ed. McGraw-Hill, New York, pp. 693–734 (1989); and, Lipson et al., *J. Clin. Invest.*, 66, 188–193 (1980)). A growing body of evidence now suggests that vascular disorders found in one-third of the patients with premature arterial disease or cerebrovascular disease are the result of mild hyperhomocysteinemia some of which may be due to heterozygous CBS deficiency (Boers et al., *N. Engl. J. Med.*, 313, 709715 (1985); and, Clarke et al., *N. Sngl. J. Med.*, 324, 1149–1155 (1991)). In addition, the CBS gene maps to human chromosome 21 at q 22.3 (Munke et al., *Am. J. Hum. Genet.*, 42, 550–559 (1988)). This region of chromosome 21 is evidently associated with many Down syndrome features; microduplications in this region precipitate many of the features associated with Down phenotype (Korenberg et al., *Am. J. Hum. Genet.*, 43, A110 (1988); and, Korenberg et al., *A. J. Hum. Genet.*, 47, 236–246 (1990)). Since the coding region of human CBS has not heretofore been determined, it is necessary to determine its sequence prior to detecting mutations in patients with CBS deficiency. Also, only through recombinant techniques can large quantities of CBS be made available as replacement enzyme to treat patients suffering from homocystinuria and other diseases resulting from CBS deficiency.

Therefore, a need arose to purify and isolate DNA sequences of CBS for evaluation of mutations in patients and for obtaining CBS in large quantities. One way to isolate a DNA sequence encoding CBS is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resultant gene library is comprised of a population of transformed host cells, each of which contain a single cDNA or cDNA fragment. The entire library, therefore, provides a representative sample of the coding information present in the mRNA mixture used as a starting material.

cDNA libraries are screened using specific nucleic acid or antibody probes. Nucleic acid probes are useful for locating cDNAs by hybridization and autoradiography techniques. This approach, however, requires previous knowledge of at least a portion of the protein's amino acid or DNA-encoding sequence. Alternatively, methods have been developed to identify specific clones by probing recombinant cDNA libraries with antibodies specific for the encoded protein of interest. This method can be used with "expression vector" cloning vehicles since elaboration of the product protein is required. An example of this is the bacteriophage λ-gt11 system described by Young and Davis, *Proc. Natl. Acad. Sci.*, 80, 1194–1198 (1983).

Once the cDNA is purified and isolated, the full length cDNA sequence can be used for insertion into expression vectors. This leads to the production of active enzyme.

SUMMARY OF THE INVENTION

In general, the invention concerns a purified and isolated DNA sequence encoding human cystathionine β-synthase. The invention also concerns cells transformed with this DNA sequence, and purified and isolated human cystathionine β-synthase encoded by this DNA sequence. The invention can permit large scale production of human cystathionine β-synthase in prokaryotic or eukaryotic expression systems. The resulting human cystathionine β-synthase can be purified and isolated by conventional techniques. Further, the invention concerns a composition, suitable for treating a human suffering from homocystinuria, containing human cystathionine β-synthase, in a pharmacologically acceptable carrier.

The invention also features methods of screening human patients to detect mutations in the cystathionine β-synthase gene. One method involves detecting a mutation on an allele of a human patient suffering from homocystinuria by identifying the mutation on the allele. Another method involves detecting a mutation in a cystathionine β-synthase cDNA sequence of a human patient suffering from homocystinuria by first determining the cDNA sequence from the patient and then comparing the patient cDNA sequence with the cDNA sequence of active cystathionine β-synthase.

In another aspect, the invention features the use of a purified and isolated cDNA sequence to synthesize cystathionine β-synthase for use in the treatment of individuals determined to have homocystinuria.

BRIEF DESCRIPTION OF THE DRAWINGS

FIGS. 1A, 1B and 1C (SEQ ID NO:1) represent the nucleotide sequence of the cloned human CBS cDNA and predicted amino acid sequence;

FIG. 3 shows the screening for synonymous mutations in CBS cDNA;

DETAILED DESCRIPTION OF THE INVENTION

Figure 2:
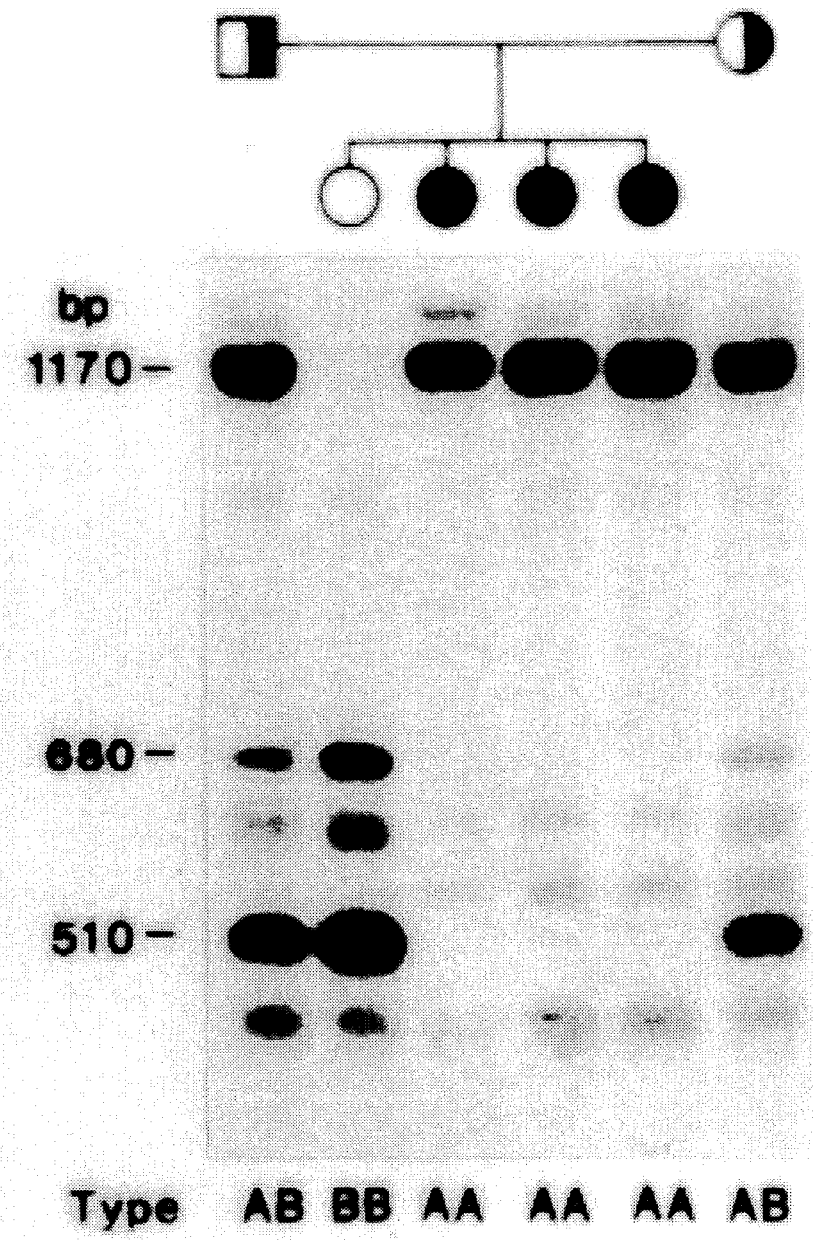
FIG. 2 represents a Southern blotting analysis showing the human CBS Msp I polymorphism.

The present invention provides a purified and isolated DNA sequence that encodes CBS. Also provided by the present invention is a synthetically produced CBS that has a biological activity of the CBS protein produced from purified DNA sequences through an in vitro expression system. The purified and isolated DNA sequence encoding CBS can be carried on vectors which can be propagated in cells. The purified and isolated DNA sequence is defined as a DNA sequence isolated from its natural environment (e.g., cDNA or genomic DNA) which hybridizes to the CBS gene under hybridizing conditions.

Purification and isolation of the recombinantly expressed protein may be obtained by conventional means, e.g., preparative chromatographic separations and immunological separations involving monoclonal and/or polyclonal antibody preparations.

"Expression vectors" refer to vectors which are capable of replicating and transcribing DNA sequences contained therein, where such sequences are linked to other regulatory sequences capable of affecting their expression. These expression vectors must be propagated in the host organisms or systems either as autonomous episomes or as an integral part of the chromosomal DNA.

The cDNA clone can be identified in the human liver library by antibodies capable of recognizing the polypeptide being produced or by hybridization with DNA probes. One form of expression vector used in recombinant DNA techniques is the prokaryotic plasmid: an unintegrated (extrachromosomal), double-stranded DNA circle. Other expression vectors are the eukaryotic vectors: vectors capable of driving expression of the foreign DNA in a eukaryotic cell. These are generally derived from viral sources and may be either extrachromosomal or integrated. The invention includes any other form of expression vector which serves an equivalent function and which is or subsequently becomes known in the art.

Recombinant vectors and methodology disclosed herein are suitable for use in a wide range of prokaryotic and eukaryotic host cells. These host cells include microbial strains, such as *E. coli, Saccharomyces cerevisiae,* baculovirus, and cell lines derived from multicellular eukaryotic organisms.

"Recombinant host cells", "host cell", "cells", "cell cultures" and so forth are used interchangeably to designate individual cells, cell lines, cell cultures, and harvested cells which have been or are intended to be transformed or transfected with the recombinant vectors of the invention. The terms also include the progeny of the cells originally receiving the vector.

"Transformed" or "transfected" refers to any process for altering the DNA content of the host. This includes in vitro transformation procedures such as calcium phosphate or DEAE-dextran-mediated transfection, electroporation, nuclear injection, phage infection, or such other means for effecting controlled DNA uptake as are known in the art.

The procedures below are but some of a wide variety of well-established procedures to produce specific reagents useful in the process of this invention. The general procedure for obtaining an mRNA mixture is to obtain a tissue sample or to culture cells producing the desired protein, and to extract the RNA by a process such as that published by Chirgwin et al., *Biochemistry,* 18, 5294 (1979). The mRNA is isolated by enriching for poly(A)-containing RNA by chromatography of the RNA on oligo(dT) cellulose or poly(U) Sepharose.

The above poly(A) containing mRNA-enriched fraction is used to synthesize a single-strand complementary cDNA (ss-cDNA) using reverse transcriptase. The second strand was synthesized by nick-translation repair Kraus et al., *Proc. Natl. Acad. Sci. USA,* 83, 2047–2051 (1986)) of the cDNA-mRNA hybrid in the presence of *Escherichia coli* enzymes: RNase H, polymerase I, and DNA ligase.

The resultant ds-cDNA is inserted into a vector by any one of many known techniques. In general, the vector is linearized by at least one restriction endonuclease, which will produce at least two blunt or cohesive ends. The ds-cDNA is ligated with (or joined into) the vector insertion site.

Prokaryotic cells are made competent by calcium chloride pretreatment and transformed with the DNA. After isolating the successfully engineered cells, the cells are cultured on selective media,and proteins encoded by the expression vector are produced.

Clones containing the cDNA for CBS are identified using appropriately specific probes that hybridize with a portion of the nucleotide sequence of CBS. The system used for cloning is the λ-gt11 system.

The present invention relates to an isolated and purified CBS cDNA sequence of 2,554 nucleotides encoding the CBS subunit of 551 amino acids. The full-length cDNA clone was isolated from a λgt 11 human liver library. The liver cDNA contained a 214 bp insert 18 bp downstream from the terminator codon (TGA). This insert, bordered by consensus splice dinucleotides GT/AG, based on the sequence of the cDNA, appeared to be an intron. The sequence of cDNA encoding human cystathionine β-synthase is depicted in FIGS. 1A, 1B and 1C (SEQ ID NO:1).

Restriction fragment length polymorphisms (RFLPs), detectable with the CBS cDNA, can aid in determining the carrier status of individuals in families with an affected homozygote. Using the human cDNA as a probe, a CBS MspI polymorphism was demonstrated in about half of the alleles. FIG. 2 shows an Italian homocystinuric family where this polymorphism is fully informative in that the absence of the MspI site segregates with the affected allele. This polymorphism is most likely identical to the one identified by single strand conformation polymorphism (46% heterozygosity) in PCR products derived from the 3'-untranslated region of CBS cDNA (Avramopoulos et al., Hum. Genet., 90, 556–568 (1993)). As shown in FIG. 2, a Southern blot (Sambrook et al., Molecular Cloning: A Laboratory Manual, 2nd Ed., Vols 1–3, Cold Spring Harbor Laboratory Press (1989)) was prepared using Msp I digested genomic DNA obtained from cultured fibroblasts of each of the individuals indicated in the figure. The blot was probed with a uniformly $^{32}$p-labeled fragment of human CBS cDNA, spanning the SphI restriction site and the 3'-terminus. Closed circles in the pedigree at the head of the figure indicate female offspring homozygous for the trait. The open circle indicates one female offspring who was homozygous normal. The half-closed circle and square indicate the heterozygous parents.

Two synonymous mutations were found while sequencing CBS cDNAs from normal individuals and patients homozygous or heterozygous for CBS deficiency. These allowed a development of a simple PCR-based method to screen for these mutations. It was employed to identify individual alleles in these subjects (FIG. 3).

PCR reactions and restriction site analyses for the Y233Y (699C/T) synonymous mutation were carried out as described in Example 2. The left panel of FIG. 3 shows the following results. Lanes 1 and 2 display analysis of the 699T allele, while lanes 3 and 4 show the analysis of the 699C allele. Odd numbered lanes contain undigested PCR products and even numbered lanes contain products after RsaI digestion. Comparison of the undigested and digested samples shows that both PCR products were completely cut at the control RsaI site as demonstrated by shortening of the 304 bp PCR product. Lane 2 contained a 280 bp fragment that was cut only at the control RsaI site and indicated that the nucleotide in position 699 is a T. PCR product in lane 4 was cut twice to a 243 bp fragment. This result demonstrated the presence of a C at position 699.

To screen for the A360A synonymous mutation (1080T/C), the PCR method and restriction site analysis was carried out as described in Example 2. The right panel of FIG. 3 shows the following results. Lane 1 and 2 show the results of one allele analysis, while lane 3 and 4 demonstrate the polymorphism at the other allele. Odd numbered lanes contain PCR products after digestion with FspI and even numbered lanes exhibit the restriction pattern after SfiI cut. PCR products were always cut by one of the enzymes thus indicating that the analysis was unequivocal. SfiI cut in lane 2 demonstrates the presence of C in position 1080 while the FspI cut in lane 3 reveals the presence of nucleotide T in the other allele.

Combined data obtained from DNA sequencing and from the PCR/restriction analysis screen are summarized in Table I below. These individuals were of varied Western European origin and no ethnic distribution pattern was observed for the synonymous mutations. This PCR method was developed solely to distinguish the paternal and maternal origin of the cloned CBS cDNAs. The PCR primers employed for this purpose span exon/exon junctions. Thus, they cannot be used to analyze genomic DNA.

TABLE I

| | Synonymous mutations in CBS cDNA | | |
|---|---|---|---|
| Mutation | Amino Acid | Restriction site | Allele frequency |
| 699C/T | Y233Y | RsaI* | 11/28 (0.39) |
| 1080C/T | A360A | FspI/SfiI | 13/23 (0.56) |

*PCR creates an RsaI site with the mismatch primer for 699C but not 699T.

Figure 4:
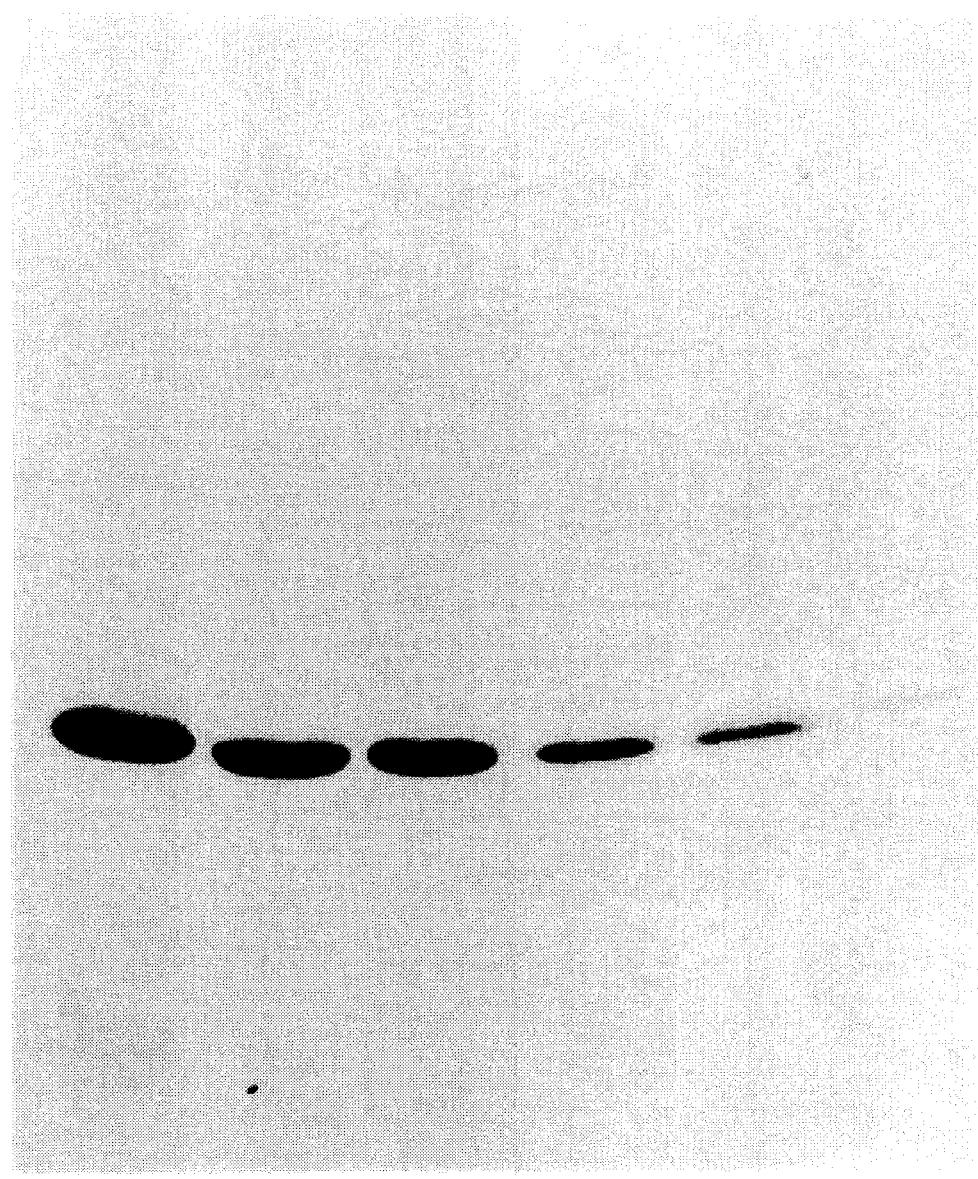
FIG. 4 shows the pulse-chase labeling of human CBS in transfected CHO cells.

To ascertain whether the cloned human cDNA encodes a functional protein, it was inserted into a methotrexate amplifiable expression vector as described previously (Roper et al., Arch. Biochem. Biophys., 298, 514–521 (1992)). The CHO cells, devoid of CBS activity (Skovby et al., Hum. Genet., 65, 291–294 (1984), were transfected with the construct and amplified in methotrexate. CBS activity was initially absent both in control CHO cells and in untreated, transfected cells. After 12 weeks of stepwise amplification in methotrexate, the specific activity increased to 53 nmols/h/mg protein, about 2–3 fold greater than the level observed in cultured human fibroblasts (Skovby et al., Am. J. Hum. Genet., 34, 73–83 (1982)). Transfected cells avidly incorporated [$^{35}$S]-L-methionine into synthase, as was apparent from the autoradiograms of labeled CBS subjected to SDS/PAGE (FIG. 4). More than 5000 cpm were found in the enzyme following 90 min uptake.

The cDNA sequence, e.g., in plasmid HSLCBS, can be used, according to the invention, to screen individuals with mutations who are homozygous or heterozygous for CBS deficiency. Such a screening method employing expression of the patient's cDNA or segments thereof can be accomplished by plasmid expression as described in Kozich and Kraus, Human Mutation, 1, 113–123 (1992). Screening for mutations can be done prenatally. Also screening can be used to detect carriers of the CBS deficiency. Such information helps evaluate the risk of passing on the disease and the severity of the disease to the carrier's offspring. In addition, the cDNA sequence, can be used, according to the invention, to produce CBS for the treatment of homocystinuria caused by a deficiency of CBS.

The following examples are presented to illustrate the present invention and to assist one of ordinary skill in making and using the same. The examples are not intended in any way to otherwise limit the scope of the invention.

EXAMPLE 1

A. Preparation of Total RNA

Total RNA was extracted from fresh frozen normal adult liver as described (Chirgwin et al., Biochemistry, 18, 5294 (1979)). Cells were homogenized in 15 volumes of a solution containing 4M guanidine thiocyanate, 25 mM sodium citrate at pH 7.0, 0.5% N-laurylsarcosine, 0.1M 2-mercaptoethanol, and 0.2% Antifoam A. The homogenate was centrifuged at 6,000×g for 15 minutes at 10° C. The supernatant fluid was adjusted to pH 5.0 by addition of acetic acid, and the RNA was precipitated by 0.75 volumes of ethanol at −20° C. overnight. RNA was collected by centrifugation and dissolved in 7.5M guanidine hydrochloride containing 25 mM sodium citrate and 5 mM dithiothreitol. Following two additional precipitations using 0.5 volumes of ethanol, the residual guanidine hydrochloride was extracted from the precipitate with absolute ethanol. RNA was dissolved in sterile water, insoluble material removed by centrifugation, and the pellets were re-extracted with water. The RNA was adjusted to 0.2M potassium acetate and precipitated by addition of 2.5 volumes of ethanol at −20° C overnight.

B. Preparation of Poly(A)-Containing RNA

The total RNA precipitate, prepared as described above, was dissolved at a concentration of 40 $A_{260}$ units per ml in 20 mM Hepes buffer at pH 7.2 containing 10 mM EDTA and 1% SDS, heated at 65° C. for 10 minutes, and then quickly cooled to 25° C. The RNA solution was then diluted with an equal volume of water, and NaCl was added to bring the final concentration to 300 mM NaCl. Samples containing up to 2400 $A_{260}$ units of RNA were chromatographed on poly(U)-SEPHAROSE using standard procedures. mRNA was eluted with 90% formamide containing 1 mM Hepes buffer (pH 7.2) and 2 mM EDTA. The eluate was adjusted to 0.24M NaCl, and the RNA was precipitated with the addition of 2.5 volumes of ethanol at −20° C.

C. Preparation of Human Liver cDNA Library in Lambda gt11 cDNA cloning was carried out according to the following protocol (Kraus et al., *Nucleic Acids Research*, 13, 943 (1985)). Briefly, cDNA was synthesized from 15 µg of human liver mRNA in a final volume of 150 µl of reaction mixture consisting of: 50mM Tris-HCl, pH 8.3, 75 mM KCl, 10 mM magnesium acetate, 4 mM DTT, 0.5 mM dATP, 0.5 mM dGTP, 0.5 mM dTTP, 0.5 mM [$\alpha$-$^{32}$P]dCTP (500 cpm/pmol), 40 µg/ml actinomycin D, 25 µg/ml oligo (dT)$_{12-18}$, 500 U/ml RNasin (Promega Biotec), 0.15 mg/ml BSA, and 120 units of reverse transcriptase (Life Sciences, Inc.). After 1 h of incubation at 44° C., another 60 units of RNasin and 48 units of reverse transcriptase were added, and the mixture was incubated for an additional hour. The reaction was terminated by addition of EDTA and NaCl to 25 mM and 100 mM, respectively, and the nucleic acids were separated from the reaction mixture on a 10 ml column of Sephadex G-150 equilibrated in 20 mM ammonium bicarbonate. The cDNA yield from mRNA was about 60%. The fractions containing the cDNA-mRNA hybrid were lyophilized.

The second strand was synthesized by nicktranslation repair (Kraus et al., *Proc. Natl. Acad. Sci. USA*, 83, 2047–2051 (1986)) of the cDNA-mRNA hybrid in the presence of *Escherichia coli* enzymes: RNase H, polymerase I, and DNA ligase. The reaction mixture (50 µl) was adjusted to contain 20 mM Tris-HCL (pH 7.5), 5 mM magnesium acetate, 10 mM ammonium sulfate, 0.1M KCl, 0.15 mM β-NAD, 60 µg of bovine serum albumin per ml, 40 µM each of the four dNTP's 2 µCi of [$\alpha$-$^{32}$P]dCTP (approx. 3000 Ci/mmol), 0.5 units of DNA ligase, 0.42 units of RNase H, and 11.5 units of DNA polymerase I. After sequential incubations at 12° C. for 1 hr. and at 22° C. for 1 hr., the ds DNA was processed as described above for the cDNA-mRNA hybrid.

The ds-cDNA was made blunt-ended by incubation with S1 nuclease. The reaction mixture consisted of 0.2 M sodium acetate (pH 4.5), 0.4M sodium chloride, 2.5 mM zinc acetate and 0.1 unit of S1 nuclease per ng of dscDNA, made to a final reaction volume of 100 µl. The dscDNA was incubated at 37° C. for one hour, extracted with phenol:chloroform, then desalted on a SEPHADEX G-50 column.

The ds-cDNA was then treated with EcoRI methylase and DNA polymerase I using reaction conditions described in Sambrook et al., *Molecular Cloning: A Laboratory Manual*, 2nd Ed., Vols 1–3, Cold Spring Harbor Laboratory Press (1989). The cDNA was again desalted on SEPHADEX G-50, and ligated to 0.5 µg of phosphorylated EcoRI linkers with T4 DNA ligase. The mixture was then cleaved with EcoRI and fractionated on an 8% acrylamide gel in Tris-Borate buffer. DNA with a size greater than 1 kilobase was eluted from the gel in 10 mM Tris (pH 7.5), 0.2M NaCl and recovered by binding to an ELUTIP-d column, eluted with 1M NaCl and then collected by ethanol precipitation.

The ds-cDNA was then inserted into EcoRI cleaved and phosphatase-treated lambda gt11 with T4 DNA ligase to produce a library of approximately twelve million phage of which 50% contain inserts (i.e., six million clear plaques on X-gal plates). The library was amplified by producing plate stocks at 42° C. on *E. coli* Y1088 [supE supF metB trpR hsdR—hsdM$^+$ tonA21 strA lacU169 proC::Tn5 (pMC9)]. Amplification procedures were as described (Kraus et al., *Proc. Natl. Acad. Sci. USA*, 83, 2047–2051 (1986)). The titer of the amplified library was determined to be 8×10$^{10}$ pfu/ml.

D. Identification of Clones Containing CBS Sequence

This library was plated at a density of 20,000 colonies per each 150 mm plate. After transferring colonies from the master plate to a nitrocellulose filter the colonies were lysed and fixed on nitrocellulose filters (Sambrook et al., *Molecular Cloning: A Laboratory Manual*, 2nd Ed., Vols 1–3, Cold Spring Harbor Laboratory Press (1989)), then hybridized with a $^{32}$p-labeled insert of p610, a rat CBS cDNA clone isolated previously (3). Three positive clones, were obtained from 720,000 colonies screened. DNA minipreps (Sambrook et al., *Molecular Cloning: A Laboratory Manual*, 2nd Ed., Vols 1–3, Cold Spring Harbor Laboratory Press (1989)) from positive clones were digested with Eco RI and analyzed on 1.2% agarose gels. The cDNA insert of a full length human CBS cDNA was subcloned into a transcription vector (pGem-3-Blue, Promega Biotec, Madison, Wis.), and the resulting construct was named HSLCBS.

E. Construction of the Expression Vector

Human CBS cDNA was cloned into pSDN, a mammalian expression plasmid conferring methotrexate resistance, essentially as described by Roper and Kraus (Roper et al., *Arch. Biochem. Biophys.*, 298, 514–521 (1992)). Human hepatic CBS cDNA spanning the entire coding reading frame and a portion of 3' untranslated sequence (2087 bp) was isolated from a pGEM Blue subclone (HSLCBS) by restriction with Hind III and Ssp I. The pSDN vector was digested with Ava I and blunt-ended with Klenow fragment of DNA polymerase; subsequently, the vector was restricted with Hind III, gel purified, ligated to the human CBS insert with T$_4$ DNA ligase. The resulting mammalian expression plasmid, pSDHCS, was used to transfect cultured CHO cells (Roper et al., *Arch. Biochem. Biophys.*, 298, 514–521 (1992)).

Figure 5:
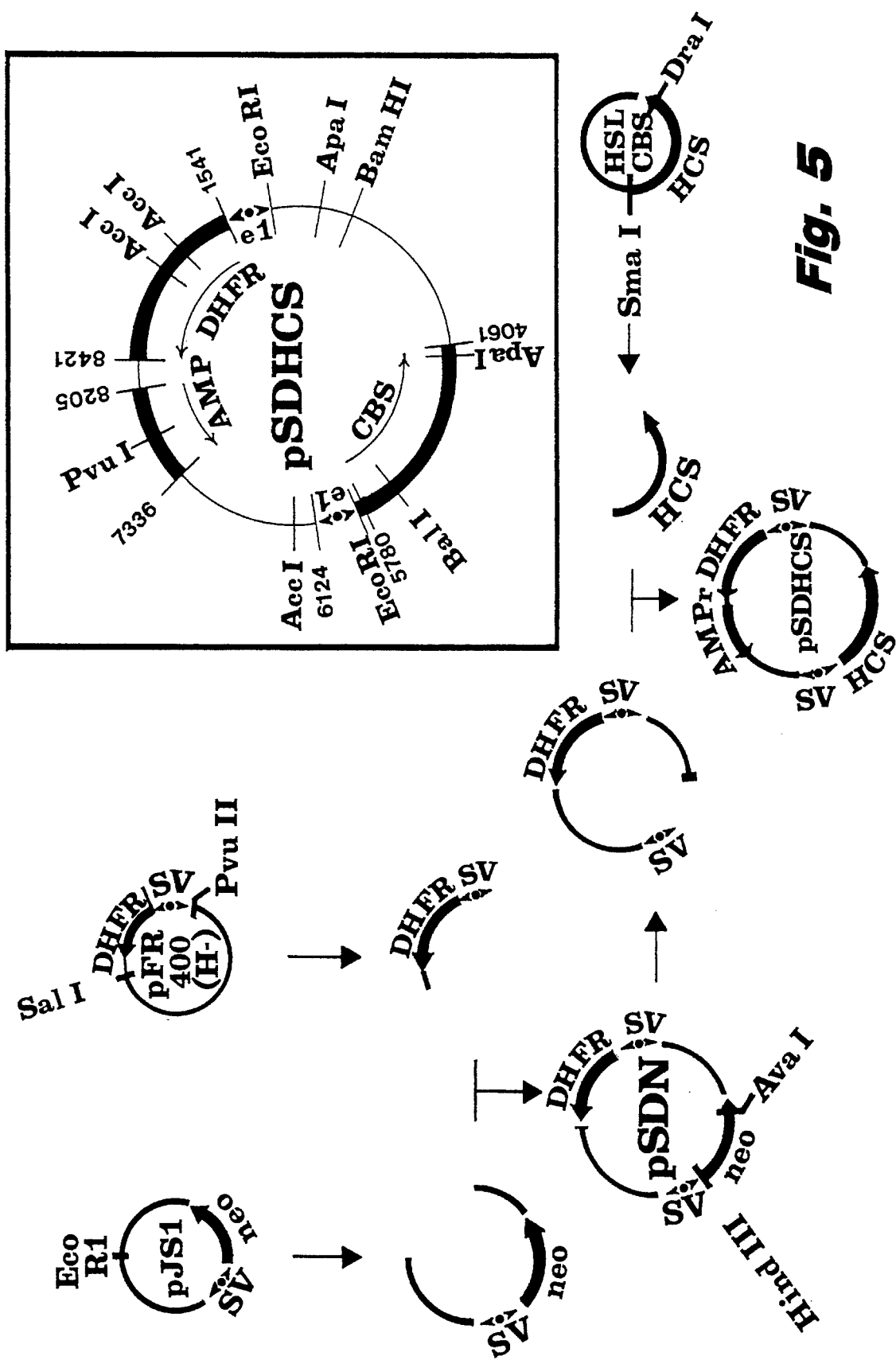
FIG. 5 is a schematic showing the strategy for the construction of the plasmid pSDHCS.

The following is a detailed description of the strategy for construction of the plasmid pSDHCS, as shown in FIG. 5. Plasmid pSDHCS was constructed from three plasmids: pJS1 (derived from pSV2neo); pFR400; and HSLCBS, human CBS in pGEM-3-Blue (Roper et al., *Arch. Biochem.*

*Biophys.*, 298, 514–521 (1992)). To generate a universal amplifiable plasmid, pSDN, the Hind III⁻ dihydrofolate reductase (DHFR) cDNA, together with its associated SV40e (early) promoter and polyadenylation signal sequence was excised from pFR400 using Pvu II/Sal I, blunt ended with Klenow fragment and inserted into the blunt-ended Eco RI site of pJS1. Colonies of transformed *E. coli* in which pSDN contained DHFR in the same orientation as neo were selected for construction of pSDHCS. Synthase cDNA was excised from HSLCBS with Sma I/Dra I. This was substituted for the majority of the neo sequence, bounded by Hind III/Ava I after the overhanging regions of the vector were backfilled with Klenow fragment. The final plasmid, pSDHCS, contained amp$^r$, derived from pJS1, SV40e-DHFR, and SV40e-CBS cDNA. A general map of plasmid pSDHCS is depicted in FIG. 5. The ◂●▸ symbols indicate the locations of the SV40 promoters with their early (e) and late (l) sites. Arrows in the inset refer to the direction of transcription for each sequence.

F. Expression of Human CBS cDNA

Dihydrofolate reductase-deficient CHO duk⁻ cells (American Type Tissue Collection #9096CRL) were transfected with 10 μg of pSDHCS in 100 μl using Lipofectin as described earlier (Roper et al., *Arch. Biochem. Biophys.*, 298, 514–521 (1992)). Clones which survived hypoxanthine/thymine starvation were isolated and incubated in increasing doses of methotrexate (1, 10, 100 μM) as described to amplify the incorporated plasmid. CBS activity was determined at each step. The enzyme as expressed had significant CBS activity of 53 nmols/h/mg protein.

CBS turnover was determined in transfected CHO cells as described earlier (Roper et al., *Arch. Biochem. Biophys.*, 298, 514–521 (1992)). Pulse-chase labeling of human CBS in transfected CHO cells is shown in FIG. 4. CHO cells, harboring methotrexate-amplified pSDHCS, were labeled with [$^{35}$S]-L-methionine (83 μCi/ml: 250 μCi/dish) for 90 min, washed, and incubated in medium supplemented with 3.75 mM unlabeled methionine. Cells were harvested starting 1 h after washing the cells to remove free labeled methionine in the medium (0 h), then at the intervals indicated on the photograph shown in FIG. 4. CBS was immunoprecipitated, electrophoresed by SDS/PAGE, and autoradiographed. Autoradiography was used to locate the dark bands, shown on the photograph in FIG. 4, which represent the labeled CBS found at each time point. These dark bands were subsequently excised from the dried gel and counted for $^{35}$S. The turnover of the enzyme was determined graphically by plotting log(% labeled CBS) vs. time following addition of unlabeled methionine.

EXAMPLE 2

Screening for Synonymous Mutations

Two synonymous mutations in the coding region of CBS cDNA (C699T; T1080C) were screened by a PCR based RFLP method described below. Template DNAs for PCR (i.e. 200–500 ng of plasmid DNAs), 1 μl of cDNAs (prepared as described [Kraus et al., *Nucleic Acids Res.* 13, 943–952 (1985)], 5 μl of bacterial cultures or a small amount of bacterial colonies, were mixed with 50 μl of water, denatured at 95° C. for 3 min (cDNA) or at 99° C. for 5 min (other templates) and rapidly chilled on ice.

The following were the conditions for PCR. Template preparations were mixed with appropriate pairs of oligonucleotide primers and other components as described previously [Tahara et al., *BioTechniques*, 8, 366–368 (1990)] using 2.5 U of Taq polymerase for each 100 μl reaction. The cycling was performed in a Hybaid thermal reactor under the following conditions: 30 cycles of denaturing at 94° C. for 1 min, annealing at 55° C. for 1 min and extension at 72° C. for 40 sec.

The screening for Y233Y synonymous mutation (699C/T) was accomplished in the following manner. The sense primer 5'-GACCAGTACCGCAACGCCAGCAAC-CCCCTGGCTCA<u>G</u>TA-3' (SEQ ID NO:3) contained at its 3' end one base pair mismatch (represented by the underlined G in place of C) that completed an RsaI site by incorporation of a C residue at the adjacent position 699. Accordingly, incorporation of a T in position 699 did not create this RsaI site. To monitor the efficiency of the digestion, another Rsa I site (underlined) was introduced into the antisense primer 5'-TTGTCCACCACCGTCCTGTCCA<u>GTAC</u>CG- 3' (SEQ ID NO: 4). Ten μl of PCR product were digested at 37° C. with 7 U of RsaI (New England Biolabs) in a total volume of 20 μl for 4 hours. These mixtures were subjected to agarose gel electrophoresis together with the uncut sample.

The screening for A360A synonymous mutation (1080C/T) was accomplished in the following manner. This screen was based on a restriction site polymorphism: nucleotide T in position 1080 was part of an FspI site while C in the same position produced an SfiI restriction site. The sense primer sequence was 5'-CGTAGAATTCAGTGGGCACGGGCG-GCACCA-3' (SEQ ID NO:5) and the antisense oligonucleotide was 5'-TACGATCGATTCTGCAGCATCCACCT-GTCGCT- 3' (SEQ ID NO:6). Five μl of PCR reaction were digested for 4 hours with either 5 U of FspI (New England Biolabs) or 5 U of SfiI (New England Biolabs) at 37° C. in the total volume of 20μl. Both digests were subsequently subjected to agarose gel electrophoresis.

EXAMPLE 3

Treatment of Patients Having a CBS Deficiency

In addition to screening, the invention includes enzyme replacement therapy for those individuals determined to have deficiency of normal CBS, and therefore, are suffering from homocystinuria.

To treat homocystinuria in these individuals, the CBS is administered therapeutically in an amount effective to prevent homocystinuria. A homocystinuria treating dosage of CBS can be determined based on the knowledge available to those of ordinary skill in the art. The CBS can be administered by injection with a pharmcologically acceptable carrier, either alone or in combination with another agent. Acceptable pharmacological carriers are those which dissolve the CBS or hold it in suspension, and which are not toxic to the extent of permanently harming the patient. Preferred are aqueous solutions of salts of non-ionic compounds such as sodium chloride or glucose, most preferably at an isotonic concentration. Other agents may be present provided they do not interfere with the action of CBS. Those skilled in the art will know, or will be able to ascertain with no more than routine experimentation, particular pharmacological carriers for this composition.

CBS suitable for therapy can be prepared by the following procedure. The CBS can be produced by expressing the CBS cDNA product from a prokaryotic or eukaryotic expression vector in an in vitro expression system, and purifying and isolating the CBS from the medium or cells of the expression system. General expression vectors and systems are well known in the art.

In addition, the CBS can be produced using protein chemistry techniques, wherein the specific amino acid residues are joined together synthetically in the appropriate sequence. The cDNA CBS sequence can be inserted into a suitable vector to be used for gene therapy.

DEPOSIT OF STRAINS USEFUL IN PRACTICING THE INVENTION

A deposit of biologically pure cultures of the following strains was made with the American Type Culture Collection, 12301 Parklawn Drive, Rockville, Md., the accession numbers indicated was assigned after successful viability testing, and the requisite fees were paid. Access to said cultures will be available during pendency of the patent application to one determined by the Commissioner to be entitled thereto under 37 C.F.R. Section 1.14 and 35 U.S.C. Section 122. All restriction on availability of said cultures to the public will be irrevocably removed upon the granting of a patent based upon the application and said cultures will remain permanently available for a term of at least five years after the most recent request for the furnishing of a sample and in any case for a period of at least 30 years after the date of the deposit. Should the cultures become nonviable or be inadvertently destroyed, they will be replaced with viable cultures of the same taxonomic description.

| Strain/Plasmid | ATCC No. | Deposit Date |
| --- | --- | --- |
| full length cDNA for human cystathione-β-synthase DH5α E. coli, HSLCBS | 69369 | July 29, 1993 |

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

What is claimed is:

1. A purified and isolated DNA sequence (SEQ ID. NO:1) encoding human cystathionine β-synthase.

2. A purified and isolated cDNA sequence consisting of a DNA encoding human cystathionine β-synthase (SEQ ID NO:2).

3. A prokaryotic or eukaryotic host cell transformed or transfected with a DNA sequence according to claim 1, 2, in an expression vector allowing the host cell to express human cystathionine β-synthase.

4. A prokaryotic or eukaryotic expression vector including a DNA sequence according to claim 1, 2, wherein the DNA sequence is linked to regulatory sequences capable of affecting the expression of the DNA sequence.

5. A prokaryotic or eukaryotic host cell stably transformed or transfected with an expression vector according to claim 4.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
  ( A ) LENGTH: 2542 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: mat_peptide
  ( B ) LOCATION: 181..1834

( i x ) FEATURE:
  ( A ) NAME/KEY: CDS
  ( B ) LOCATION: 181..1834

( x i ) SEQUENCE DESCRIPTION: SEQ ID NO:1:

```
TGCAGGGCCA  GGACGCACGT  TTCAAGCTCA  TCAGTAAAGG  TTCCTTAAAT  TCCCGAAGCA        60

AGAAGTTAAC  CAAGTAAAAC  AGCATCGGAA  CACCAGGATC  CCATGACAGA  TTCTGTTGTC       120

ACGTCTCCTT  ACAGAGTTTG  AGCGGTGCTG  AACTGTCAGC  ACCATCTGTC  CGGTCCAGC        180

ATG  CCT  TCT  GAG  ACC  CCC  CAG  GCA  GAA  GTG  GGG  CCC  ACA  GGC  TGC  CCC        228
Met  Pro  Ser  Glu  Thr  Pro  Gln  Ala  Glu  Val  Gly  Pro  Thr  Gly  Cys  Pro
 1              5                        10                       15

CAC  CGC  TCA  GGG  CCA  CAC  TCG  GCG  AAG  GGG  AGC  CTG  GAG  AAG  GGG  TCC        276
His  Arg  Ser  Gly  Pro  His  Ser  Ala  Lys  Gly  Ser  Leu  Glu  Lys  Gly  Ser
            20                       25                       30

CCA  GAG  GAT  AAG  GAA  GCC  AAG  GAG  CCC  CTG  TGG  ATC  CGG  CCC  GAT  GCT        324
Pro  Glu  Asp  Lys  Glu  Ala  Lys  Glu  Pro  Leu  Trp  Ile  Arg  Pro  Asp  Ala
            35                       40                       45

CCG  AGC  AGG  TGC  ACC  TGG  CAG  CTG  GGC  CGG  CCT  GCC  TCC  GAG  TCC  CCA        372
Pro  Ser  Arg  Cys  Thr  Trp  Gln  Leu  Gly  Arg  Pro  Ala  Ser  Glu  Ser  Pro
            50                       55                       60
```

-continued

| | | | | | | | | | | | | | | | | |
|---|---|---|---|---|---|---|---|---|---|---|---|---|---|---|---|---|
| CAT | CAC | CAC | ACT | GCC | CCG | GCA | AAA | TCT | CCA | AAA | ATC | TTG | CCA | GAT | ATT | 420 |
| His | His | His | Thr | Ala | Pro | Ala | Lys | Ser | Pro | Lys | Ile | Leu | Pro | Asp | Ile | |
| 65 | | | | 70 | | | | | 75 | | | | | | 80 | |
| CTG | AAG | AAA | ATC | GGG | GAC | ACC | CCT | ATG | GTC | AGA | ATC | AAC | AAG | ATT | GGG | 468 |
| Leu | Lys | Lys | Ile | Gly | Asp | Thr | Pro | Met | Val | Arg | Ile | Asn | Lys | Ile | Gly | |
| | | | | 85 | | | | | 90 | | | | | 95 | | |
| AAG | AAG | TTC | GGC | CTG | AAG | TGT | GAG | CTC | TTG | GCC | AAG | TGT | GAG | TTC | TTC | 516 |
| Lys | Lys | Phe | Gly | Leu | Lys | Cys | Glu | Leu | Leu | Ala | Lys | Cys | Glu | Phe | Phe | |
| | | | | 100 | | | | | 105 | | | | | 110 | | |
| AAC | GCG | GGC | GGG | AGC | GTG | AAG | GAC | CGC | ATC | AGC | CTG | CGG | ATG | ATT | GAG | 564 |
| Asn | Ala | Gly | Gly | Ser | Val | Lys | Asp | Arg | Ile | Ser | Leu | Arg | Met | Ile | Glu | |
| | | | 115 | | | | 120 | | | | | 125 | | | | |
| GAT | GCT | GAG | CGC | GAC | GGG | ACG | CTG | AAG | CCC | GGG | GAC | ACG | ATT | ATC | GAG | 612 |
| Asp | Ala | Glu | Arg | Asp | Gly | Thr | Leu | Lys | Pro | Gly | Asp | Thr | Ile | Ile | Glu | |
| 130 | | | | | 135 | | | | | | 140 | | | | | |
| CCG | ACA | TCC | GGG | AAC | ACC | GGG | ATC | GGG | CTG | GCC | CTG | GCT | GCG | GCA | GTG | 660 |
| Pro | Thr | Ser | Gly | Asn | Thr | Gly | Ile | Gly | Leu | Ala | Leu | Ala | Ala | Ala | Val | |
| 145 | | | | | 150 | | | | | 155 | | | | | 160 | |
| AGG | GGC | TAT | CGC | TGC | ATC | ATC | GTG | ATG | CCA | GAG | AAG | ATG | AGC | TCC | GAG | 708 |
| Arg | Gly | Tyr | Arg | Cys | Ile | Ile | Val | Met | Pro | Glu | Lys | Met | Ser | Ser | Glu | |
| | | | | 165 | | | | | 170 | | | | | 175 | | |
| AAG | GTG | GAC | GTG | CTG | CGG | GCA | CTG | GGG | GCT | GAG | ATT | GTG | AGG | ACG | CCC | 756 |
| Lys | Val | Asp | Val | Leu | Arg | Ala | Leu | Gly | Ala | Glu | Ile | Val | Arg | Thr | Pro | |
| | | | 180 | | | | | 185 | | | | | 190 | | | |
| ACC | AAT | GCC | AGG | TTC | GAC | TCC | CCG | GAG | TCA | CAC | GTG | GGG | GTG | GCC | TGG | 804 |
| Thr | Asn | Ala | Arg | Phe | Asp | Ser | Pro | Glu | Ser | His | Val | Gly | Val | Ala | Trp | |
| | | 195 | | | | | 200 | | | | | 205 | | | | |
| CGG | CTG | AAG | AAC | GAA | ATC | CCC | AAT | TCT | CAC | ATC | CTA | GAC | CAG | TAC | CGC | 852 |
| Arg | Leu | Lys | Asn | Glu | Ile | Pro | Asn | Ser | His | Ile | Leu | Asp | Gln | Tyr | Arg | |
| | 210 | | | | | 215 | | | | | 220 | | | | | |
| AAC | GCC | AGC | AAC | CCC | CTG | GCT | CAC | TAC | GAC | ACC | ACC | GCT | GAT | GAG | ATC | 900 |
| Asn | Ala | Ser | Asn | Pro | Leu | Ala | His | Tyr | Asp | Thr | Thr | Ala | Asp | Glu | Ile | |
| 225 | | | | | 230 | | | | | 235 | | | | | 240 | |
| CTG | CAG | CAG | TGT | GAT | GGG | AAG | CTG | GAC | ATG | CTG | GTG | GCT | TCA | GTG | GGC | 948 |
| Leu | Gln | Gln | Cys | Asp | Gly | Lys | Leu | Asp | Met | Leu | Val | Ala | Ser | Val | Gly | |
| | | | | 245 | | | | | 250 | | | | | 255 | | |
| ACG | GGC | GGC | ACC | ATC | ACG | GGC | ATT | GCC | AGG | AAG | CTG | AAG | GAG | AAG | TGT | 996 |
| Thr | Gly | Gly | Thr | Ile | Thr | Gly | Ile | Ala | Arg | Lys | Leu | Lys | Glu | Lys | Cys | |
| | | | 260 | | | | | 265 | | | | | 270 | | | |
| CCT | GGA | TGC | AGG | ATC | ATT | GGG | GTG | GAT | CCC | GAA | GGG | TCC | ATC | CTC | GCA | 1044 |
| Pro | Gly | Cys | Arg | Ile | Ile | Gly | Val | Asp | Pro | Glu | Gly | Ser | Ile | Leu | Ala | |
| | | 275 | | | | | 280 | | | | | 285 | | | | |
| GAG | CCG | GAG | GAG | CTG | AAC | CAG | ACG | GAG | CAG | ACA | ACC | TAC | GAG | GTG | GAA | 1092 |
| Glu | Pro | Glu | Glu | Leu | Asn | Gln | Thr | Glu | Gln | Thr | Thr | Tyr | Glu | Val | Glu | |
| | 290 | | | | | 295 | | | | | 300 | | | | | |
| GGG | ATC | GGC | TAC | GAC | TTC | ATC | CCC | ACG | GTG | CTG | GAC | AGG | ACG | GTG | GTG | 1140 |
| Gly | Ile | Gly | Tyr | Asp | Phe | Ile | Pro | Thr | Val | Leu | Asp | Arg | Thr | Val | Val | |
| 305 | | | | | 310 | | | | | 315 | | | | | 320 | |
| GAC | AAG | TGG | TTC | AAG | AGC | AAC | GAT | GAG | GAG | GCG | TTC | ACC | TTT | GCC | CGC | 1188 |
| Asp | Lys | Trp | Phe | Lys | Ser | Asn | Asp | Glu | Glu | Ala | Phe | Thr | Phe | Ala | Arg | |
| | | | | 325 | | | | | 330 | | | | | 335 | | |
| ATG | CTG | ATC | GCG | CAA | GAG | GGG | CTG | CTG | TGC | GGT | GGC | AGT | GCT | GGC | AGC | 1236 |
| Met | Leu | Ile | Ala | Gln | Glu | Gly | Leu | Leu | Cys | Gly | Gly | Ser | Ala | Gly | Ser | |
| | | | 340 | | | | | 345 | | | | | 350 | | | |
| ACG | GTG | GCG | GTG | GCC | GTG | AAG | GCT | GCG | CAG | GAG | CTG | CAG | GAG | GGC | CAG | 1284 |
| Thr | Val | Ala | Val | Ala | Val | Lys | Ala | Ala | Gln | Glu | Leu | Gln | Glu | Gly | Gln | |
| | | | 355 | | | | | 360 | | | | | 365 | | | |
| CGC | TGC | GTG | GTC | ATT | CTG | CCC | GAC | TCA | GTG | CGG | AAC | TAC | ATG | ACC | AAG | 1332 |
| Arg | Cys | Val | Val | Ile | Leu | Pro | Asp | Ser | Val | Arg | Asn | Tyr | Met | Thr | Lys | |
| 370 | | | | | 375 | | | | | 380 | | | | | | |

| | | | | | | | | | | | | | | | | |
|---|---|---|---|---|---|---|---|---|---|---|---|---|---|---|---|---|
| TTC | CTG | AGC | GAC | AGG | TGG | ATG | CTG | CAG | AAG | GGC | TTT | CTG | AAG | GAG | GAG | 1380 |
| Phe 385 | Leu | Ser | Asp | Arg | Trp 390 | Met | Leu | Gln | Lys 395 | Gly | Phe | Leu | Lys | Glu | Glu 400 | |
| GAC | CTC | ACG | GAG | AAG | AAG | CCC | TGG | TGG | TGG | CAC | CTC | CGT | GTT | CAG | GAG | 1428 |
| Asp | Leu | Thr | Glu | Lys 405 | Lys | Pro | Trp | Trp | Trp 410 | His | Leu | Arg | Val | Gln 415 | Glu | |
| CTG | GGC | CTG | TCA | GCC | CCG | CTG | ACC | GTG | CTC | CCG | ACC | ATC | ACC | TGT | GGG | 1476 |
| Leu | Gly | Leu | Ser 420 | Ala | Pro | Leu | Thr | Val 425 | Leu | Pro | Thr | Ile | Thr 430 | Cys | Gly | |
| CAC | ACC | ATC | GAG | ATC | CTC | CGG | GAG | AAG | GGC | TTC | GAC | CAG | GCG | CCC | GTG | 1524 |
| His | Thr | Ile 435 | Glu | Ile | Leu | Arg | Glu 440 | Lys | Gly | Phe | Asp | Gln 445 | Ala | Pro | Val | |
| GTG | GAT | GAG | GCG | GGG | GTA | ATC | CTG | GGA | ATG | GTG | ACG | CTT | GGG | AAC | ATG | 1572 |
| Val | Asp 450 | Glu | Ala | Gly | Val | Ile 455 | Leu | Gly | Met | Val | Thr 460 | Leu | Gly | Asn | Met | |
| CTC | TCG | TCC | CTG | CTT | GCC | GGG | AAG | GTG | CAG | CCG | TCA | GAC | CAA | GTT | GGC | 1620 |
| Leu 465 | Ser | Ser | Leu | Leu | Ala 470 | Gly | Lys | Val | Gln | Pro 475 | Ser | Asp | Gln | Val | Gly 480 | |
| AAA | GTC | ATC | TAC | AAG | CAG | TTC | AAA | CAG | ATC | CGC | CTC | ACG | GAC | ACG | CTG | 1668 |
| Lys | Val | Ile | Tyr | Lys 485 | Gln | Phe | Lys | Gln | Ile 490 | Arg | Leu | Thr | Asp | Thr 495 | Leu | |
| GGC | AGG | CTC | TCG | CAC | ATC | CTG | GAG | ATG | GAC | CAC | TTC | GCC | CTG | GTG | GTG | 1716 |
| Gly | Arg | Leu | Ser 500 | His | Ile | Leu | Glu | Met 505 | Asp | His | Phe | Ala | Leu 510 | Val | Val | |
| CAC | GAG | CAG | ATC | CAG | TAC | CAC | AGC | ACC | GGG | AAG | TCC | AGT | CAG | CGG | CAG | 1764 |
| His | Glu | Gln 515 | Ile | Gln | Tyr | His | Ser 520 | Thr | Gly | Lys | Ser | Ser 525 | Gln | Arg | Gln | |
| ATG | GTG | TTC | GGG | GTG | GTC | ACC | GCC | ATT | GAC | TTG | CTG | AAC | TTC | GTG | GCC | 1812 |
| Met | Val 530 | Phe | Gly | Val | Val | Thr 535 | Ala | Ile | Asp | Leu | Leu 540 | Asn | Phe | Val | Ala | |
| GCC | CAG | GAG | CGG | GAC | CAG | AAG | T GAAGTCCGGA GCGCTGGGCG GTGTGGAGCG | | | | | | | | | 1864 |
| Ala 545 | Gln | Glu | Arg | Asp | Gln 550 | Lys | | | | | | | | | | |

| | | | | |
|---|---|---|---|---|
| GGCCCGCCAC | CCTTGCCCAC | TTCTCCTTCG | CTTTCCTGAG | CCCTAAACAC ACGCGTGATT | 1924 |
| GGTAACTGCC | TGGCCTGGCA | CCGTTATCCC | TGCACACGGC | ACAGAGCATC CGTCTCCCCT | 1984 |
| CGTTAACACA | TGGCTTCCTA | AATGGCCCTG | TTTACGGCCT | ATGAGATGAA ATATGTGATT | 2044 |
| TTCTCTAATG | TAACTTCCTC | TTAGGATGTT | TCACCAAGGA | AATATTGAGA GAGAAGTCGG | 2104 |
| CCAGGTAGGA | TGAACACAGG | CAATGACTGC | GCAGAGTGGA | TTAAAGGCAA AAGAGAGAAG | 2164 |
| AGTCCAGGAA | GGGGCGGGGA | GAAGCCTGGG | TGGCTCAGCA | TCCTCCACGG GCTGCGCGTC | 2224 |
| TGCTCGGGGC | TGAGCTGGCG | GGACGAGTTT | GCGTGTTTGG | GTTTTTAAT TGAGATGAAA | 2284 |
| TTCAAATAAC | CTAAAAATCA | ATCACTTGAA | AGTGAACAAT | CAGCGGCATT TAGTACATCC | 2344 |
| AGAAAGTTGT | GTAGGCACCA | CCTCTGTCAC | GTTCTGGAAC | ATTCTGTCAT CACCCCGTGA | 2404 |
| AGCAATCATT | TCCCCTCCCG | TCTTCCTCCT | CCCCTGGCAA | CTGCTGTCGA CTTTGTGTCT | 2464 |
| CTGTTGTCTA | AAATAGGTTT | TCCCTGTTCT | GGACATTTCA | TATAAATGGA ATCACACAAA | 2524 |
| AAAAAAAAAA | AAAAAAA | | | | 2542 |

( 2 ) INFORMATION FOR SEQ ID NO:2:

( i ) SEQUENCE CHARACTERISTICS:
        ( A ) LENGTH: 551 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Met 1 | Pro | Ser | Glu | Thr 5 | Pro | Gln | Ala | Glu | Val 10 | Gly | Pro | Thr | Gly | Cys 15 | Pro |
| His | Arg | Ser | Gly 20 | Pro | His | Ser | Ala | Lys 25 | Gly | Ser | Leu | Glu | Lys 30 | Gly | Ser |
| Pro | Glu | Asp 35 | Lys | Glu | Ala | Lys | Glu 40 | Pro | Leu | Trp | Ile | Arg 45 | Pro | Asp | Ala |
| Pro | Ser 50 | Arg | Cys | Thr | Trp | Gln 55 | Leu | Gly | Arg | Pro | Ala 60 | Ser | Glu | Ser | Pro |
| His 65 | His | His | Thr | Ala | Pro 70 | Ala | Lys | Ser | Pro | Lys 75 | Ile | Leu | Pro | Asp | Ile 80 |
| Leu | Lys | Lys | Ile | Gly 85 | Asp | Thr | Pro | Met | Val 90 | Arg | Ile | Asn | Lys | Ile 95 | Gly |
| Lys | Lys | Phe | Gly 100 | Leu | Lys | Cys | Glu | Leu 105 | Leu | Ala | Lys | Cys | Glu 110 | Phe | Phe |
| Asn | Ala | Gly 115 | Gly | Ser | Val | Lys | Asp 120 | Arg | Ile | Ser | Leu | Arg 125 | Met | Ile | Glu |
| Asp | Ala 130 | Glu | Arg | Asp | Gly | Thr 135 | Leu | Lys | Pro | Gly | Asp 140 | Thr | Ile | Ile | Glu |
| Pro 145 | Thr | Ser | Gly | Asn | Thr 150 | Gly | Ile | Gly | Leu | Ala 155 | Leu | Ala | Ala | Ala | Val 160 |
| Arg | Gly | Tyr | Arg | Cys 165 | Ile | Ile | Val | Met | Pro 170 | Glu | Lys | Met | Ser | Ser 175 | Glu |
| Lys | Val | Asp | Val 180 | Leu | Arg | Ala | Leu | Gly 185 | Ala | Glu | Ile | Val | Arg 190 | Thr | Pro |
| Thr | Asn | Ala 195 | Arg | Phe | Asp | Ser | Pro 200 | Glu | Ser | His | Val | Gly 205 | Val | Ala | Trp |
| Arg | Leu 210 | Lys | Asn | Glu | Ile | Pro 215 | Asn | Ser | His | Ile | Leu 220 | Asp | Gln | Tyr | Arg |
| Asn 225 | Ala | Ser | Asn | Pro | Leu 230 | Ala | His | Tyr | Asp | Thr 235 | Thr | Ala | Asp | Glu | Ile 240 |
| Leu | Gln | Gln | Cys | Asp 245 | Gly | Lys | Leu | Asp | Met 250 | Leu | Val | Ala | Ser | Val 255 | Gly |
| Thr | Gly | Gly | Thr 260 | Ile | Thr | Gly | Ile | Ala 265 | Arg | Lys | Leu | Lys | Glu 270 | Lys | Cys |
| Pro | Gly | Cys 275 | Arg | Ile | Ile | Gly | Val 280 | Asp | Pro | Glu | Gly | Ser 285 | Ile | Leu | Ala |
| Glu | Pro 290 | Glu | Glu | Leu | Asn | Gln 295 | Thr | Glu | Gln | Thr | Thr 300 | Tyr | Glu | Val | Glu |
| Gly 305 | Ile | Gly | Tyr | Asp | Phe 310 | Ile | Pro | Thr | Val | Leu 315 | Asp | Arg | Thr | Val | Val 320 |
| Asp | Lys | Trp | Phe | Lys 325 | Ser | Asn | Asp | Glu | Glu 330 | Ala | Phe | Thr | Phe | Ala 335 | Arg |
| Met | Leu | Ile | Ala 340 | Gln | Glu | Gly | Leu | Leu 345 | Cys | Gly | Gly | Ser | Ala 350 | Gly | Ser |
| Thr | Val | Ala 355 | Val | Ala | Val | Lys 360 | Ala | Ala | Gln | Glu | Leu 365 | Gln | Glu | Gly | Gln |
| Arg | Cys 370 | Val | Val | Ile | Leu | Pro 375 | Asp | Ser | Val | Arg | Asn 380 | Tyr | Met | Thr | Lys |
| Phe 385 | Leu | Ser | Asp | Arg | Trp 390 | Met | Leu | Gln | Lys | Gly 395 | Phe | Leu | Lys | Glu | Glu 400 |
| Asp | Leu | Thr | Glu | Lys 405 | Lys | Pro | Trp | Trp | Trp 410 | His | Leu | Arg | Val | Gln 415 | Glu |
| Leu | Gly | Leu | Ser | Ala 420 | Pro | Leu | Thr | Val | Leu 425 | Pro | Thr | Ile | Thr | Cys 430 | Gly |

| His | Thr | Ile<br>435 | Glu | Ile | Leu | Arg | Glu<br>440 | Lys | Gly | Phe | Asp | Gln<br>445 | Ala | Pro | Val |
| Val | Asp<br>450 | Glu | Ala | Gly | Val | Ile<br>455 | Leu | Gly | Met | Val | Thr<br>460 | Leu | Gly | Asn | Met |
| Leu<br>465 | Ser | Ser | Leu | Leu | Ala<br>470 | Gly | Lys | Val | Gln | Pro<br>475 | Ser | Asp | Gln | Val | Gly<br>480 |
| Lys | Val | Ile | Tyr | Lys<br>485 | Gln | Phe | Lys | Gln | Ile<br>490 | Arg | Leu | Thr | Asp | Thr<br>495 | Leu |
| Gly | Arg | Leu | Ser<br>500 | His | Ile | Leu | Glu | Met<br>505 | Asp | His | Phe | Ala | Leu<br>510 | Val | Val |
| His | Glu | Gln<br>515 | Ile | Gln | Tyr | His | Ser<br>520 | Thr | Gly | Lys | Ser | Ser<br>525 | Gln | Arg | Gln |
| Met | Val<br>530 | Phe | Gly | Val | Val | Thr<br>535 | Ala | Ile | Asp | Leu | Leu<br>540 | Asn | Phe | Val | Ala |
| Ala<br>545 | Gln | Glu | Arg | Asp | Gln<br>550 | Lys | | | | | | | | | |

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GACCAGTACC GCAACGCCAG CAACCCCCTG GCTCAGTA 38

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTGTCCACCA CCGTCCTGTC CAGTACCG 28

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CGTAGAATTC AGTGGGCACG GGCGGCACCA 30

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA (xi) SEQUENCE DESCRIPTION: SEQ ID NO:6:

TACGATCGAT TCTGCAGCAT CCACCTGTCG CT                    32